US 6,696,051 B2

(12) United States Patent
Barbuzzi et al.

(10) Patent No.: US 6,696,051 B2
(45) Date of Patent: Feb. 24, 2004

(54) HAIR TREATMENT COMPOSITIONS

(75) Inventors: Elena Maria Gabriella Barbuzzi, Merseyside (GB); Wolfgang Robert Bergmann, Chicago, IL (US); David Howard Birtwistle, Bangkok (TH); Cheryl Anne Taylor, Merseyside (GB); Stephen Lee Wire, Merseyside (GB)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 0 days.

(21) Appl. No.: 10/136,041

(22) Filed: Apr. 30, 2002

(65) Prior Publication Data

US 2003/0095943 A1 May 22, 2003

(30) Foreign Application Priority Data

Apr. 30, 2001 (EP) .............................. 01303916

(51) Int. Cl.$^7$ ................................ A61K 7/075
(52) U.S. Cl. ................. 424/70.12; 424/70.1; 424/70.27
(58) Field of Search ............................ 424/70.1, 70.12, 424/70.27

(56) References Cited

U.S. PATENT DOCUMENTS 4,801,445 A    1/1989   Fukui et al.

FOREIGN PATENT DOCUMENTS

| EP | 0224978 A2 | 6/1987 |
| EP | 0478326 A1 | 4/1992 |
| WO | 01/30310 | 5/2001 |

OTHER PUBLICATIONS

Harry's Cosmeticology, pp 506–508, (1982).*

U.S. patent application Ser. No. 10/114,622, filed May 6, 1998, Japan–English translation enclosed.

European Search Report Application No. EP 01 30 3915 dated Dec. 13, 2001.

Chemical Abstracts, vol. 129, No. 1, (7/98) to Matsumoto et al. "cosmetic Stock compositions for Hair Preparation and Skin Makeup"—XP 002185547 & JP 10 114622 A assigned to Toshiba Silicone Co.

* cited by examiner

*Primary Examiner*—Jyothsna Venkat
(74) *Attorney, Agent, or Firm*—Milton L. Honig

(57) ABSTRACT

This invention relates to an aqueous conditioner composition comprising (i) a cationic surfactant, (ii) a fatty alcohol material, and (iii) from 0.01 to 10 wt % coated particles comprising (a) a solid core having a D3,2 average particle size in the range from 10 to 700 nm, and (b) a coating of silicone polymer covalently bonded to the solid core. Use of the coated particles in a conditioner composition to impart body to the hair is also disclosed.

7 Claims, No Drawings

HAIR TREATMENT COMPOSITIONS

FIELD OF THE INVENTION

This invention relates to rinse-off hair conditioner compositions and to their use in the treatment of hair.

BACKGROUND AND PRIOR ART

Shampoo compositions are generally formulated with highly effective cleansing surfactants, typically anionic surfactants, and do not in themselves provide much conditioning or styling benefit to the hair. In fact, basic shampoo formulations which have not been supplemented with specific conditioning or styling agents have a tendency to leave the hair in a cosmetically-unsatisfactory condition with regards to manageability and stylability. The hair tends to have a harsh, dull and dry feel, often referred to as "creak", is often difficult to comb, in either the wet or the dry state, typically has poor brushing properties, and tends to have poor set-retaining abilities.

This has resulted in the use of products containing specific conditioning and/or styling agents. Such agents are generally applied separately after shampooing and rinsing the hair, for example, in the form of conditioner formulations or styling mousses etc.

Conventional conditioner formulations, although providing substantial improvements in for example the wet and dry combing properties of the hair and in the smoothness of the hair, do not in themselves impart styling attributes such as body and volume to the hair. If fact, conventional conditioners tend to have a negative effect on many of the attributes associated with hair body.

One of the most common methods for imparting styling benefits to the hair has been the use of hair fixative agents, such as high molecular weight polymers. The problem with using such agents is that they have a tendency to negatively impact on conditioning attributes such as wet and dry stage clean feel and smoothness. In fact, they can result in a sticky feel to the hair.

Conventional styling polymers are typically water soluble. This means that when incorporated into a conditioner which is rinsed off the hair, there is a tendency for the styling polymer to be washed away to a greater or lesser degree with the conditioner. Hence, most styling products are leave-in products which are applied to the hair as post-conditioner treatments.

The problem being addressed by the present invention is the provision of rinse-off conditioner compositions which impart styling benefits, and in particular body benefits on the hair, but which do not negatively impact on the conditioning benefits imparted by the conditioner. The body benefits or attributes the present invention is looking particularly to provide are root lift, increased hair volume, bounce, control (i.e. ease of styling) and manageability, i.e. maintenance of style without undue stiffness and negative sensory feel. Such body attributes are particularly attractive to people with fine or long, weighty hair.

One approach that has been taken to address this problem has been the use different forms of styling agents such as small particulate materials. Such an approach is described, for example, in our unpublished PCT International Patent Application No. PCT/GB00/04020. This document describes the use of small hard particles, and in particular colloidal silica, in hair treatment compositions to impart body and volume to the hair. Although providing significant styling benefits, the use of these materials can still lead to small levels of sensory negatives, such as for example a dry feel to the hair.

We have now found that the inclusion of a certain level of small solid particles covalently grafted with a silicone polymer in conventional conditioner formulations provides substantial styling benefits, in particular with regards to imparting body attributes to the hair. Furthermore, the conditioning attributes of conditioner compositions containing these particles are not compromised. The compositions are also stable.

JP 10144622 (Toshiba Silicone) discloses cosmetic compositions containing from 0.5 to 50 wt % of particles consisting of colloidal silica cores surrounded by silicone shells which may be used on the skin or hair. Hairdressing lotions, hair creams and cleansing compositions such as a shampoo, rinse and conditioner are disclosed as suitable cosmetic compositions in which the particles can by utilised. In the treatment of hair, they are described as providing a flexible and smooth feeling and as having good set-retaining ability. There is no teaching that the particles provide significant body benefits, such as volume, root lift and bounce, to the hair.

Although JP 10144622 discloses that the core-shell particles may be used in a shampoo composition, only nonionic surfactants are identified as being useful additional surfactant components when making up cosmetic compositions comprising the particles. Nonionic surfactants are also disclosed as improving the stability of the cosmetic compositions. Anionic surfactants and cationic surfactants are discussed at length with respect to pre-emulsification of the particles, but there is no mention of and no examples demonstrating the inclusion of such surfactants as additional components when making up the cosmetic compositions. Example 13 in JP 10144622 describes a shampoo composition comprising 20 wt % nonionic surfactant, less than 0.01 wt % anionic surfactant and more than 1 wt % core-shell particles.

We have found that the incorporation of the small particles covalently grafted with silicone polymer into conventional conditioner compositions leads to substantive improvements in the body of the conditioned hair, especially if a subsequent styling regime is followed. The compositions impart body attributes, such as are root lift, volume, bounce and manageability, in the absence (or substantial absence) of a styling polymer, which leads to compositions which have a styling benefit, but nevertheless do not suffer from the sensory negatives (e.g. stickiness and/or dry feel) which are associated with prior styling compositions which are based on, for example, a styling polymer.

DEFINITION OF THE INVENTION

Accordingly, this invention provides an aqueous conditioner composition comprising (i) a cationic surfactant;
(ii) a fatty alcohol material; and
(iii) from 0.01 to 10 wt % of coated particles comprising
   (a) a solid core having a $D_{3,2}$ average particle size in the range from 10 to 700 nm, and
   (b) a coating of silicone polymer covalently bonded to the solid core.

Additionally, this invention provides for use of coated particles as defined above in a conditioner composition to impart body to hair.

DETAILED DESCRIPTION AND PREFERRED EMBODIMENTS

Definitions

Unless specified otherwise, all wt % values quoted hereinafter are percentages by weight based on total weight of the conditioner composition.

As used hereinafter, the term "coated particle" refers to a particle comprising a solid core having a D3,2 average particle size in the range 10 to 700 nm which is coated, via covalent grafting, with a silicone polymer, the polymer forming a coating or shell around the solid core.

As used hereinafter, the term "solid core" or "solid core particle" refers to the solid core of the coated particle.

As used hereinafter, the term "coating polymer" or "polymer coating" refers to the silicone polymer covalently grafted to the solid core of the coated particle.

As used hereinafter, the term "water-insoluble", means that the material is soluble in distilled water at a concentration of less than 0.01 g/l, preferably less than 0.001 g/l at 20° C.

As used hereinafter, the term "aggregates" refers to secondary particles which are a collection of primary particles which have been fused to form face to face sintered structures which cannot be dissociated, and as such are relatively hard.

$D_{3,2}$ average droplet or particle sizes as referred to herein may be measured by means of a laser light scattering technique, using a 2600D Particle Sizer from Malvern Instruments.

Coated Particles

The coated particles are present in the conditioner composition in an amount of from 0.01 to 10, preferably from 0.01 to 5, more preferably from 0.05 to 3, yet more preferably from 0.05 to 2.5, and most preferably from 0.1 to 1 wt %. In particular, it has been found that levels of coated particles of 0.5 wt % or less work particularly well in the compositions of the present invention.

The coated particles comprise solid cores having D3,2 average particle sizes in the range from 10 to 700 nm, the solid cores being coated with a silicone polymer which is covalently bonded to the solid core.

Preferably, the D3,2 average particle size of the coated particles is in the range from 20 to 1000, more preferably from 20 to 800, yet more preferably from 50 to 500 and most preferably from 50 to 250 nm.

Sufficient silicone is grafted so as to form a effective shell around the solid core. Suitably, the weight ratio of the solid core to the silicone coating polymer is in the range from 20:1 to 1:10, preferably from 20:1 to 2:3, more preferably from 20:1 to 1:1, more preferably from 10:1 to 1:1, yet more preferably from 5:1 to 1:1, and most preferably from 5:1 to 2:1. A particularly preferred ratio is about 4:1.

Although coated particles that are sparingly soluble may be employed in conditioner compositions of the invention, it is highly preferred that the coated particles be water-insoluble.

Solid Core

The solid core particles have a D3,2 average particle size in the range from 10 to 700, preferably from 10 to 500, more preferably from 20 to 300, yet more preferably from 20 to 200, and most preferably from 30 to 150 nm, for example about from 50 to 100 nm.

It is preferred that the solid core particles be colloidal in an aqueous dispersion.

The solid core can be a primary particle or an aggregate, so long as its satisfies the size requirement specified above. Preferably, it is a primary particle.

Suitably, the solid core particles are relatively hard and typically have a Youngs Modulus of more than 0.01, preferably more than 0.1, more preferably more than 1.0, yet more preferably more than 4 GPa, and yet more preferably more than 10 GPa.

The solid core material can be organic or inorganic in nature. Furthermore, the solid core may be composed entirely of one material or may consist of a composite of materials.

Suitable organic solid particles can be made by a variety of methods including:

(i) via the synthesis of (co)polymers as described in, for example, Breiner et al. (1998) *Macromolecules*, Vol. 31, 135; and (ii) via the synthesis of cross-linked polymer structures as described in, for example:
Ishizu & Fukutomi (1988) *J. Polym. Sci.*, Part C: *Polym. Lett.*, Vol. 26, 281;
Saito et al. (1990) *Polymer*, Vol. 31, 679;
Thurmond et al. (1997) *J. Am. Chem. Soc.*, Vol. 119, 6656; and
Stewart & Liu (2000) *Agnew. Chem. Int. Ed.*, Vol. 39, 340).

Suitable inorganic solid particles can be prepared by techniques such as:

(i) precipitation, as described in, for example, Matjievic (1993) *Chem. Mater.*, Vol. 5, 412;

(ii) dispersion, as described in, for example, Stober et al. (1968) *J. Colloid Interface Sci.*, Vol. 26, 62; and Philipse & Vrij (1989) *J. Colloid Interface Sci.*, Vol. 129, 121);

(iii) microemulsion processes, as described in, for example, Baumann et al. (1997) *Adv. Mater.*, Vol. 9, 995; and (iv) sol-gel processes, as described in, for example:
Forster & Antonietti (1998) *Adv. Mater.*, Vol. 10, 195;
Kramer et al. (1998) *Langmuir*, Vol. 14, 2027;
Hedrick et al. (1998) *Adv. Mater.*, Vol. 10, 1049;
Zhao et al. (1998) D. *Science*, Vol. 279, 548; and
Ulrich et al. (1999) *Adv. Mater.*, Vol. 11, 141.

Examples of suitable solid core materials for use as the solid cores include polymers, which are preferably cross-linked, (e.g. polystyrene, silicone elastomer powders, PTFE, rubber), silicas, alumina, alumin silicate, clays and colloidal metals (e.g. titanium dioxide, zinc oxide).

One preferred class of material is PTFE. PTFE solid core particles may be composed entirely of PTFE polymer or may consist of a composite of PTFE polymer and one or more further polymers such as polyethylene. Suitable PTFE particles are further described in our unpublished copending United Kingdom Patent Application Nos. GB 0012064.2 and GB 0012061.8.

Another preferred class of materials are silicas, such as silica gels, hydrated silicas and precipitated silicas (e.g. Cab-O-Sil and Aerosil).

A particularly preferred class of solid core materials are the colloidal silicas. Suitable examples include Ludox HS-40, Ludox SM, Ludox CL and Ludox AM.

Suitably, the solid core amounts to from 95 to 5 wt %, preferably from 95 to 40, more preferably from 90 to 50, and most preferably from 90 to 60 wt %, for example about 80 wt %, of the total weight of the coated particles.

Solid cores that are either water-insoluble or only sparingly soluble in water may be employed in the preparation of coated particles. Preferably, the solid core is water-insoluble.

Coating Polymer

The coating polymer is a silicone polymer which is covalently bonded to the solid core.

Suitably, the coating polymer amounts to from 5 to 95, preferably from 10 to 60, more preferably from 10 to 50, and most preferably from 10 to 40 wt %, for example about 20 wt %, of the total weight of the coated particles.

Suitably, the molecular weight of the coating polymer is no greater than 500,000, preferably no greater than 250,000, more preferably no greater than 200,000, yet more preferably no greater than 150,000 and yet more preferably no greater than 100,000 Daltons. The molecular weight may be lower than 50,000 or even lower than 25,000 Daltons.

Suitably, the molecular weight is at least 500, preferably at least 1,000, more preferably at least 2,000 and yet more preferably at least 5,000 Daltons.

The silicone polymer is tethered to the surface of the solid core particle by one or more covalent bonds, although other secondary means of attachment such as hydrogen bonding and absorption may also be present. The silicone polymer may be bonded via its terminal end(s) and/or via side-chains in the polymer chain. Preferably at least 70 wt %, more preferably at least 80 wt % and yet more preferably at least 90 wt % of the silicone polymer present in coating on the solid core is covalently bonded to the solid core surface.

More than one silicone polymer may be used to coat the solid core.

Suitable silicone polymers for use as the coating polymer are polyorganosiloxanes represented by the formula I:

$$R^1_a SiO_{(4-a)/2} \quad (I)$$

in which

R$^1$ is a hydrogen atom or a substituted or unsubstituted hydrocarbon group; and a is 1.80–2.20.

Examples of suitable unsubstituted hydrocarbon groups include (i) linear or branched C1–20 alkyls group; (ii) aryl groups such as benzyl, β-phenylethyl, methylbenzyl and naphthylmethyl groups; and (iii) cycloalkyl groups such as cyclohexyl and cyclopentyl.

Examples of suitable substituted hydrocarbon groups include (i) groups where hydrogen atom(s) of the above-mentioned unsubstituted hydrocarbon groups is/are substituted with halogen atom(s) such as fluorine or chlorine, for example 3,3,3-trifluoropropyl and fluoropropyl groups; (ii) groups containing an ethylenic unsaturated group; and (iii) groups containing an organic functional group containing at least one oxygen or nitrogen atoms.

Suitable organic functional groups include:

—CH$_2$CH$_2$CH$_2$NH$_2$
—CH$_2$CH$_2$CH$_2$NHCH$_2$CH$_2$NH$_2$
—CH$_2$CH$_2$CH$_2$NHCH$_2$CH$_2$NHCH$_2$CH$_2$NH$_2$

 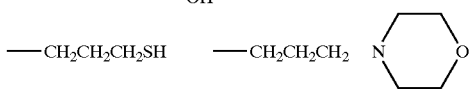

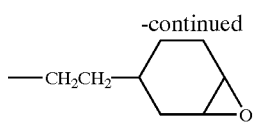

Suitable ethylenic unsaturated groups include the following, in which n is an integer from 0 to 10:

(a) CH$_2$=CH—O—(CH$_2$)$_n$
suitable examples being vinyloxyethyl and vinyloxyethoxy groups, and preferably vinyloxypropyl and vinyloxyethoxypropyl groups;

(b) CH2=CH—(CH2)$_n$
suitable examples being homoallyl, 5-hexenyl and 7-octenyl groups, and preferably vinyl and allyl groups;

(c)

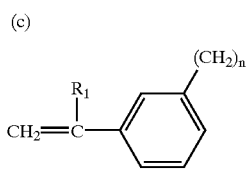

in which

R$^1$ is a hydrogen atom or a C1–6 alkyl group, preferably a hydrogen atom or methyl group.

Suitable examples include (vinylphenyl)methyl, isopropenylvinylphenyl, 2-(vinylphenoxy)ethyl, 3-(vinylbenzoyloxy)propyl, 3-(isopropenylbenzoylkoxy) propyl, and 3-(isopropenylbenzoyloxy)propyl groups. Preferred groups are vinylphenyl, 1-(vinylphenyl)ethyl and 2-(vinylphenyl)ethyl groups;

(d)

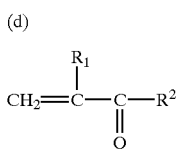

in which

R$^2$ is a C1–6 alkylene group or a group represented by the formula

—O—, S— or —N(R$^3$)R$^4$— where

R$^3$ is a C1–6 hydrocarbon or a (meth)acryloyl group, and
R$^4$ is a C1–6 alkylene group.

Suitable examples include γ-acryloxypropyl, γ-methacrylaoxypropyl and N,N-bis(methacryloyl)-γ-aminopropyl groups. Preferred groups are N-methacryloyl-N-methyl-γ-aminopropyl and N-acryloyl-N-methyl-γ-aminopropyl groups.

Preparation of Coated Particles

The coated particles are preferably prepared as an aqueous pre-emulsion, which can then be mixed with other ingredients to form the conditioner composition.

Different methods of preparation may be used depending of the size of coated particles required. Suitably, the coated particles can be prepared as follow:

(i) "Large" Coated Particles

Larger coated particles, for example having a D3,2 average particle size of at least 100 nm and which employ solid core particles having D3,2 average particle size of at least 50 nm, can be prepared in an aqueous polymerisation system in which the solid core particles are mixed with water, an emulsifying surfactant, an organosiloxane component and a suitable polymerisation catalyst. The resulting aqueous emulsion of coated particles can be directly incorporated into a conditioner composition.

(ii) "Small" Coated Particles

Smaller coated particles, for example having a D3,2 average particle size of less than 100 nm and which employ solid core particles having D3,2 average particle size of less than 50 nm, tend to have to be prepared by an alternative organic polymerisation system in which the solid core particles are mixed with an organosiloxane component in an organic solvent, free of any surfactant. The resulting coated particles are typically precipitated out of the organic solvent, washed and redispersed in water as an aqueous emulsion with a suitable emulsifying surfactant.

Organosiloxane Units

The silicone coating polymer is suitably prepared by polymerisation of component monomers or oligomers. Typically, the solid core particles are mixed with organosiloxane units having 2–10 silicon atoms and containing no hydroxyl groups and being of unit formula (II):

$$R^1{}_n SiO_{(4-n)/2} \tag{II}$$

in which

R$^1$ is a hydrogen atom or a substituted or unsubstituted hydrocarbon group.

A cross-linking agent such as a silane compound having a functional group may be added to the organosiloxane component for the silicone coat so as to improve the strength of the polymer shell.

Examples of suitable organosiloxane component units from which the polyorganosiloxane coating polymer is formed by the condensation reaction are as follows:

(i) Cyclic compounds such as hexamethyl cyclotrisiloxane, octamethyl cyclotetrasiloxane, decamethyl cyclopentasiloxane, 1,3,5,7-tetramethyl-1,3,5,7-tetraphenyl cyclotetrasiloxane, 1,3,5,7-tetrabenzyltetramethyl cyclotetrasiloxane and 1,3,5,7-tris(3,3,3-trifluoropropyl)trimethylsiloxane;

(ii) Cyclic organosiloxanes containing an organic functional group such as trimethyl triphenyl cyclotrisiloxane, tris(3,3,3-aminopropyl) tetramethyl cyclotetrasiloxane, 1,3,5,7-tetra[N-(2-aminoethyl)-3-aminopropyl] tetramethyl cyclotetrasiloxane, 1,3,5,7,-tetra(3-mercaptopropyl) tetramethyl cyclotetrasiloxane and 1,3,5,7,-tetra(3glycidoxypropyl) tetramethyl cyclotetrasiloxane.

(iii) Cyclic and linear organosiloxanes having an ethylenically unsaturated group such as 1,3,5,7-tetra(3-methacryloxypropyl) tetramethyl cyclotetrasiloxane, 1,3,5,7-tetra(3-acryloxypropyl) tetramethyl cyclotetrasiloxane, 1,3,5,7-tetra(3-carboxypropyl) tetramethyl cyclotetrasiloxane, 1,3,5,7-tetra (vinyloxypropyl) tetramethyl cyclotetrasiloxane, 1,3,5,7,-tetra(vinyloxyethoxypropyl) tetramethyl tetracyclosiloxane, 1,3,5,7-tetra(p-vinylphenyl) tetramethyl cyclotetrasiloxane, 1,3,5,7,-tetra[1-(m-vinylphenyl)methyl] tetramethyl cyclotetrasiloxane, 1,3,5,7,-tetra[2(p-vinylphenyl)ethyl] tetramethyl cyclotetrasiloxane, 1,3,5,7-tetra[3-(p-vinylphenoxy) propyl] tetramethyl cyclotetrasiloxane, 1,3,5,7,-tetra[3-(p-vinylbenzoyloxy)propyl tetramethyl tetracyclosilaoxane, 1,3,5,7,-tetrea[3-(p-isopropenylbenzoylamino)propyl] tetramethyl tetracyclosiloxane, 1,3,5,7,-tetra(N-methacryloyl-N-methyl-3-aminopropyl) tetramethyl cyclotetrasiloxane, 1,3,5,7,-tetra(N-acryloyl-N-methyl-3-aminopropyl) tetramethyl cyclotetrasiloxane, 1,3,5,7,-tetra[N,N-bis(methacryloyl)-3-aminopropyl] tetramethyl cyclotetrasiloxane, 1,3,5,7-tetra[N,N-bis(acryloyl)-3-aminopropyl] tetramethyl cyclotetrasiloxane, 1,3,5,7-tetravinyl tetramethyl cyclotetrasiloxane, octavinyl cyclotetrasiloxane, 1,3,5-trivinyl trimethyl cyclotrisiloxane, 1,3,5,7-tetraallyl tetramethyl cyclotetrasiloxane, 1,3,5,7-tetra(5-hexenyl) tetramethyl cyclotetrasiloxane, 1,3,5,7-tetra(7-oxenyl) tetramethyl cyclotetrasiloxane and 1-(p-vinylphenyl)-1,1-diphenyl-3-diethoxy disiloxane.

Examples of suitable silane compounds which may be added to the organosiloxane component for the silicone coat so as to improve the strength of the polymer shell are as follows:

(i) Silane compounds having an organic functional group such as 3-aminopropylmethyl dimethoxysilane, 3-aminopropyltrimethoxysilane, N-(2-aminoethyl-3-aminopropyl trimethoxysilane, N-triethylenediaminepropylmethyl dimethoxysilane, 3-glycidoxypropylmethyl dimethoxysilane, 3,4-epoxycyclohexylethyl trimethoxysilane, 3-mercaptopropyl trimethoxysilane, trifluoropropyl trimethoxysilane and 3-carboxypropylmethyl dimethoxysilane.

(ii) Silane compounds having an ethylenic unsaturated group such as 3-acryloxypropyl triethoxysilane, 3-methacryloxypropyl trimethoxysilane, (vinyloxypropyl)methyl dimethoxysilane, (vinyloxyethoxypropyl)methyl dimethoxysilane, p-vinylphenylmethyl dimethoxysilane, 1-(m-vinylphenyl)methyldimethyl isopropoxysilane, 2-(p-vinylphenyl)ethyldimethoxysilane, 3-(p-vinylphenoxy) propylmethyl dimethoxysilane, 1-(p-vinylphenyl) ethylmethyl methoxysilane, 1-(o-vinylphenyl)-1,1,2-trimethyldimethoxydisilane, m-vinylphenyl[(3-triethoxysilyl)propl] diphenylsilane, [3-(p-isopropenylbenzoylamino)propyl] diphenyldipropoxysilane, N-methacryloyyl-N-methyl-3-aminopropylmethyl dimethoxysilane, N-acryloyl-N-methyl-3-aminopropylmethyl dimethoxysilane, N,N-bis(methacryloyl)-3-aminopropyl methoxysilane, N,N-bis(acryloyl)-3-aminopropylmethyl dimethoxysilane, N-methacryloyl-N-methyl-3-aminopropylphenyl diethoxysilane, 1-methacryloylpropyl01,1,3-trimethyl-3,3-dimethoxydisiloxane, vinylmethyl dimethoxysilane, vinylethyl diisoproposysilane, allylmethyl dimethoxysilane, 5-hexenylmethyl diethoxysilane and 3-octenylethyl diethoxysilane.

Any of the organosiloxanes or silanes can be used either singly or as a mixture of two or more organosiloxanes and/or silanes.

Besides the above-mentioned silicones, linear or branched organosiloxane oligomers may also be used as an organosiloxane containing an organic functional group or an ethylenic unsaturated group. In the case of such organosiloxane oligomers, although there is no particular limitation for the terminal group of the molecular chain terminal is sequestered by an organic group other than a hydroxyl group such as an alkoxy group, trimethylsilyl group, dimethylvinylsilyl group, methylphenylvinylsilyl group, methyldiphenylsilyl group and 3,3,3-trifluoropropyldimethylsilyl group.

Emulsifying Surfactant

Any surfactant materials either alone or in admixture may be used as emulsifiers in the preparation of the pre-emulsions of coated particles. Suitable emulsifiers include anionic, cationic and nonionic emulsifiers.

Examples of anionic emulsifiers are alkylarylsulphonates, e.g., sodium dodecylbenzene sulphonate, alkyl sulphates e.g., sodium, lauryl sulphate, alkyl ether sulphates, e.g., sodium lauryl ether sulphate nEO, where n is from 1 to 20 alkylphenol ether sulphates, e.g., octylphenol ether sulphate nEO where n is from 1 to 20, and sulphosuccinates, e.g., sodium dioctylsulphosuccinate.

Suitable cationic surfactants are well-known to the person skilled in the art. Preferably, the cationic surfactant contains a quaternary ammonium group. Suitable examples of such cationic surfactants are described hereinbelow in the section on co-surfactants. Particularly preferred as cationic emulsifying surfactants are C6–20, preferably C8–18, monoalkyl and dialkyl quaternary ammonium compounds.

Examples of nonionic emulsifiers are alkylphenol ethoxylates, e.g., nonylphenol ethoxylate nEO, where n is from 1 to 50, alcohol ethoxylates, e.g., lauryl alcohol nEO, where n is from 1 to 50, ester ethoxylates, e.g., polyoxyethylene monostearate where the number of oxyethylene units is from 1 to 30.

Preferably, at least one anionic surfactant or cationic surfactant is present as an emulsifying surfactant.

(i) Aqueous Polymerisation System

In this process, the solid core particles are mixed with water, an emulsifying surfactant, an organosiloxane component and a suitable polymerisation catalyst. Preferred methods for preparing coated particles according to this system are described in JP 10114622.

Any catalyst may be used so long as it is capable of polymerising a low-molecular organosiloxane in the presence of water. Suitable catalysts include those commonly used for polymerisation of low-molecular organosiloxanes such as a mixture of hydroxylated aliphatic sulphonic acid with an unsaturated aliphatic sulphonic acid, an aliphatic hydrogen sulphate, an aliphatic substituted benzenesulphonic acid, hydrochloric acid, sulphuric acid, phosphoric acid.

Certain anionic surfactant emulsifiers have a weak catalytic action such can be used in conjunction with a polymerisation catalyst. Such anionic surfactants include sodium dodecylbenzenesulphonate, sodium octylbenzenesulphonate, ammonium dodecylbenzenesulphonate, sodium lauryl sulphate, ammonium lauryl sulphate, triethanolamine lauryl sulphate, sodium tetradecenesulphonate and sodium hydroxytetradecenesulphonate.

Cationic surfactant emulsifiers can also have a weak catalytic action and, therefore, it is preferred to use them together with a polymerization catalyst such as an alkaline metal hydroxide (e.g., lithium hydroxide, sodium hydroxide, potassium hydroxide, potassium hydroxide, rubidium hydroxide and caesium hydroxide).

The amount of water used in the emulsification is typically from 50 to 500, preferably from 100 to 300 parts by weight to 100 parts by weight of the total amount of the coated particles component in the emulsion. The solid concentration in the emulsion is typically from 20 to 70, preferably from 30 to 60 wt % of the total weight of the emulsion. The temperature of preparation of the emulsion (i.e. for the condensation reaction) is typically in the range from 5 to 100° C.

The amount of emulsifying surfactant in the emulsification is typically from 0.5 to 50, preferably from 0.5 to 20 parts by weight of the total amount of the coated particles component in the emulsion.

The amount of polymerization catalyst in the emulsification is typically from 0.05 to 10 parts by weight of the total amount of the coated particles component in the emulsion.

As already mentioned, a preferred solid core material of the present invention is colloidal silica. In the emulsification step, this is present as an aqueous dispersion with $SiO_2$ as the basic unit of the solid core particles. Ordinarily, colloidal silica is classified into acidic and alkaline subclasses based upon its characteristics and any of them may be appropriately selected and used depending upon the condition for the emulsification polymerisation. When using acidic silica, the emulsifying surfactant should be an anionic surfactant, and conversely, when using an alkaline silica, the emulsifying surfactant should be a cationic surfactant, in order to keep the silica in a stable state.

In a preferred embodiment, the emulsifying surfactant is an cationic surfactant. Thus when using silica as the solid core, preferably alkaline silica is used. The coated particle emulsion prepared using cationic surfactant as the emulsifying agent has been found to produce conditioner formulations which are more stable.

(ii) Organic Polymerisation System

In this process, the solid core particles are mixed with an organosiloxane component in an organic solvent, free of any surfactant. The resulting coated particles are typically precipitated out of the organic solvent, washed and redispersed in water with a suitable emulsifying surfactant to form an aqueous emulsion. Preferred methods for preparing coated particles according to this system are described in Pyun et al. (2001) *Polym. Prepr.* (*Am. Chem. Soc., Div. Polym. Chem.*), Vol. 42(1), 223.

A suitable method for preparing "smaller" coated particles, for example in which the solid core particles have a D3,2 average particle size of 10 to 20 nm. is a microemulsion process. An example of a suitable microemulsion process for the preparation of silica solid cores coated with silicone polymer is as follows. Silica colloid is prepared in an aqueous medium (e.g. 6 mM NaOH) by the reaction of methyltrimethoxysilane within micelles in the presence of an emulsifying surfactant (e.g. a quaternary ammonium cationic surfactant). The presence of the surfactant around the particles prevents large-scale flocculation. In order to prevent the colloid particles aggregating via residual surface silanol groups, the surface silanol groups of the silica colloid are silylised. Firstly, whilst still in the aqueous medium, surface silanol groups are reacted with methoxytrimethylsilane to generate trimethylsilyl groups. The particles are then precipitated into an appropriate organic solvent (e.g. methanol) to remove the surfactant, and subsequently redispersed in an appropriate organic solvent (e.g. tetrahydofurnan). The transfer from aqueous to organic solvent is necessary to achieve complete silylisation of the surface silanol groups and thus obtain stable colloids. Any residual silanol groups are deactivated and 2-bromoisobutyrate groups incorporated onto the surface of the particles by reacting the colloid particles in an appropriate organic solvent with 3-(2-bromoisobutyryloxy)-propylchlorodimethylsilane and 1,1,1,3,3,-hexamethyldisilazane. The functionalised silica colloids can then be purified by precipitation, e.g. in methanol, and dialysis in acetone. The functionalised silica colloids are then coated by reaction with organosiloxane units in an atom transfer radical polymerisation (ATRP) to form coated particles.

The coated particles are finally precipitated out of the organic solvent, for example, into methanol, washed (e.g. with acetone) and redispersed in water with a suitable emulsifying surfactant to form an aqueous pre-emulsion of coated particles.

Preferably, whatever method of preparation is used, the emulsifying surfactant present in the aqueous pre-emulsion of coated particles is a cationic surfactant.

The pre-emulsions of the coated particles have a tendency to be either acidic or alkaline in nature. In order to keep them stable over a long period, they are neutralised by adding alkali or acid. Examples of suitable alkali neutralising agents are sodium hydroxide, thorium carbonate, thorium bicarbonate and triethanolamine. Examples of suitable acidic neutralising agents are hydrochloric acid, sulphuric acid, nitric acid, acetic acid and oxalic acid.

Conditioner Compositions

Compositions of the invention are formulated as conditioners for the treatment of hair (typically after shampooing) and subsequent rinsing.

Conditioning Surfactant

The conditioner compositions of the present invention comprise one or more conditioning surfactants which are cosmetically acceptable and suitable for topical application to the hair.

Suitable conditioning surfactants are selected from cationic surfactants, used singly or in admixture.

Cationic surfactants useful in compositions of the invention contain amino or quaternary ammonium hydrophilic moieties which are positively charged when dissolved in the aqueous composition of the present invention.

Examples of suitable cationic surfactants are those corresponding to the general formula:

$$[N(R_1)(R_2)(R_3)(R_4)]^+ (X)^-$$

in which $R_1$, $R_2$, $R_3$, and $R_4$ are independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halogen, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

The most preferred cationic surfactants for conditioner compositions of the present invention are monoalkyl quaternary ammonium compounds in which the alkyl chain length is C8 to C14.

Suitable examples of such materials correspond to the general formula:

$$[N(R_5)(R_6)(R_7)(R_8)]^+ (X)^-$$

in which $R_5$ is a hydrocarbyl chain having 8 to 14 carbon atoms or a functionalised hydrocarbyl chain with 8 to 14 carbon atoms and containing ether, ester, amido or amino moieties present as substituents or as linkages in the radical chain, and $R_6$, $R_7$ and $R_8$ are independently selected from (a) hydrocarbyl chains of from 1 to about 4 carbon atoms, or (b) functionalised hydrocarbyl chains having from 1 to about 4 carbon atoms and containing one or more aromatic, ether, ester, amido or amino moieties present as substituents or as linkages in the radical chain, and X is a salt-forming anion such as those selected from halogen, (e.g. chloride, bromide), acetate, citrate, lactate, glycolate, phosphate nitrate, sulphate, and alkylsulphate radicals.

The functionalised hydrocarbyl chains (b) may suitably contain one or more hydrophilic moieties selected from alkoxy (preferably $C_1$–$C_3$ alkoxy), polyoxyalkylene (preferably $C_1$–$C_3$ polyoxyalkylene), alkylamido, hydroxyalkyl, alkylester, and combinations thereof.

Preferably the hydrocarbyl chains $R_1$ have 12 to 14 carbon atoms, most preferably 12 carbon atoms. They may be derived from source oils which contain substantial amounts of fatty acids having the desired hydrocarbyl chain length. For example, the fatty acids from palm kernel oil or coconut oil can be used as a source of C8 to C12 hydrocarbyl chains.

Typical monoalkyl quaternary ammonium compounds of the above general formula for use in shampoo compositions of the invention include:

(i) lauryl trimethylammonium chloride (available commercially as Arquad C35 ex-Akzo); cocodimethyl benzyl ammonium chloride (available commercially as Arquad DMCB-80 ex-Akzo)

(ii) compounds of the general formula:

$$[N(R_1)(R_2)((CH_2 CH_2 O)_x H)((CH_2 CH_2 O)_y H)]^+ (X)^-$$

in which:

x+y is an integer from 2 to 20;

$R_1$ is a hydrocarbyl chain having 8 to 14, preferably 12 to 14, most preferably 12 carbon atoms or a functionalised hydrocarbyl chain with 8 to 14, preferably 12 to 14, most preferably 12 carbon atoms and containing ether, ester, amido or amino moieties present as substituents or as linkages in the radical chain;

$R_2$ is a $C_1$–$C_3$ alkyl group or benzyl group, preferably methyl, and

X is a salt-forming anion such as those selected from halogen, (e.g. chloride, bromide), acetate, citrate, lactate, glycolate, phosphate nitrate, sulphate, methosulphate and alkylsulphate radicals.

Suitable examples are PEG-n lauryl ammonium chlorides (where n is the PEG chain length), such as PEG-2 cocomonium chloride (available commercially as Ethoquad C12 ex-Akzo Nobel); PEG-2 cocobenzyl ammonium chloride (available commercially as Ethoquad CB/12 ex-Akzo Nobel); PEG-5 cocomonium methosulphate (available commercially as Rewoquat CPEM ex-Rewo); PEG-15 cocomonium chloride (available commercially as Ethoquad C/25 ex-Akzo); PEG-2 oleamonium chloride (available commercially as Ethoquad O/12 PG ex Akzo Nobel).

(iii) compounds of the general formula:

$$(N(R_1)(R_2)(R_3)((CH_2)_n OH))^+ (X)^-$$

in which:

n is an integer from 1 to 4, preferably 2;

$R_1$ is a hydrocarbyl chain having 8 to 14, preferably 12 to 14, most preferably 12 carbon atoms;

$R_2$ and $R_3$ are independently selected from $C_1$–$C_3$ alkyl groups, and are preferably methyl, and X is a salt-forming anion such as those selected from halogen, (e.g. chloride, bromide), acetate, citrate, lactate, glycolate, phosphate nitrate, sulphate, and alkylsulphate radicals.

Suitable examples are lauryldimethylhydroxyethylammonium chloride (available commercially as Prapagen HY ex-Clariant)

Mixtures of any of the foregoing cationic surfactants compounds may also be suitable.

Examples of suitable cationic surfactants include:

quaternary ammonium chlorides, e.g. alkyltrimethylammonium chlorides wherein the alkyl group has from about 8 to 22 carbon atoms, for example octyltrimethylammonium chloride, dodecyltrimethylammonium chloride, hexadecyltrimethylammonium chloride, cetyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallow trimethylammonium chloride, cocotrimethylammonium chloride, and the corresponding salts thereof, e.g., bromides, hydroxides. Cetylpyridinium chloride or salts thereof, e.g., chloride Quaternium -5

Quaternium -31

Quaternium -18 and mixtures thereof.

In the conditioners of the invention, the level of cationic surfactant is preferably from 0.01 to 10, more preferably 0.05 to 5, most preferably 0.1 to 2 wt % of the total composition.

Fatty Alcohol Material

The conditioner compositions of the invention additionally comprise a fatty alcohol material. The combined use of fatty alcohol materials and cationic surfactants in conditioning compositions is believed to be especially advantageous, because this leads to the formation of a lamellar phase, in which the cationic surfactant is dispersed.

By "fatty alcohol material" is meant a fatty alcohol, an alkoxylated fatty alcohol, or a mixture thereof.

Representative fatty alcohols comprise from 8 to 22 carbon atoms, more preferably 16 to 20. Examples of suitable fatty alcohols include cetyl alcohol, stearyl alcohol and mixtures thereof. The use of these materials is also advantageous in that they contribute to the overall conditioning properties of compositions of the invention.

Alkoxylated, (e.g. ethoxylated or propoxylated) fatty alcohols having from about 12 to about 18 carbon atoms in the alkyl chain can be used in place of, or in addition to, the fatty alcohols themselves. Suitable examples include ethylene glycol cetyl ether, polyoxyethylene (2) stearyl ether, polyoxyethylene (4) cetyl ether, and mixtures thereof.

The level of fatty alcohol material in conditioners of the invention is suitably from 0.01 to 15, preferably from 0.1 to 10, and more preferably from 0.1 to 5 wt %. The weight ratio of cationic surfactant to fatty alcohol is suitably from 10:1 to 1:10, preferably from 4:1 to 1:8, optimally from 1:1 to 1:7, for example 1:3.

Optional Ingredients

Compositions of this invention may contain any other ingredients normally used in conditioner formulations. These other ingredients may include additional conditioning agents, viscosity modifiers, suspending agents, preservatives, colouring agents, polyols such as glycerine and polypropylene glycol, chelating agents such as EDTA, antioxidants, fragrances, antimicrobials and sunscreens. Each of these ingredients will be present in an amount effective to accomplish its purpose. Generally these optional ingredients are included individually at a level of up to 5 wt % of the total composition.

Cationic Polymers

The compositions according to the present invention may comprise a cationic polymer for enhancing conditioning performance of the conditioner.

The cationic polymer may be a homopolymer or be formed from two or more types of monomers. The molecular weight of the polymer will generally be between 5 000 and 10 000 000, typically at least 10 000 and preferably in the range 100 000 to about 2 000 000. The polymers will have cationic nitrogen containing groups such as quaternary ammonium or protonated amino groups, or a mixture thereof.

The cationic nitrogen-containing group will generally be present as a substituent on a fraction of the total monomer units of the cationic polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give a polymer having a cationic charge density in the required range.

Suitable cationic conditioning polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1–C7 alkyl groups, more preferably C1–3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

The cationic conditioning polymers can comprise mixtures of monomer units derived from amine- and/or quaternary ammonium-substituted monomer and/or compatible spacer monomers.

Suitable cationic conditioning polymers include, for example:

copolymers of 1-vinyl-2-pyrrolidine and 1-vinyl-3-methyl-imidazolium salt (e.g. chloride salt), referred to in the industry by the Cosmetic, Toiletry, and Fragrance Association, (CTFA) as Polyquaternium-16. This material is commercially available from BASF Wyandotte Corp. (Parsippany, N.J., USA) under the LUVIQUAT tradename (e.g. LUVIQUAT FC 370);

copolymers of 1-vinyl-2-pyrrolidine and dimethylaminoethyl methacrylate, referred to in the industry (CTFA) as Polyquaternium-11. This material is available commercially from Gaf Corporation (Wayne, N.J., USA) under the GAFQUAT tradename (e.g., GAFQUAT 755N);

cationic diallyl quaternary ammonium-containing polymers including, for example, dimethyldiallyammonium chloride homopolymer and copolymers of acrylamide and dimethyldiallylammonium chloride, referred to in the industry (CTFA) as Polyquaternium 6 and Polyquaternium 7, respectively;

mineral acid salts of amino-alkyl esters of homo-and co-polymers of unsaturated carboxylic acids having from 3 to 5 carbon atoms, (as described in U.S. Pat. No. 4,009,256);

cationic polyacrylamides(as described in WO95/22311).

Other cationic conditioning polymers that can be used include cationic polysaccharide polymers, such as cationic cellulose derivatives, cationic starch derivatives, and cationic guar gum derivatives. Suitably, such cationic polysaccharide polymers have a charge density in the range from 0.1 to 4 meq/g.

Cationic polysaccharide polymers suitable for use in compositions of the invention include those of the formula:

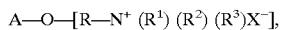

A—O—[R—N$^+$ (R$^1$) (R$^2$) (R$^3$)X$^-$], wherein: A is an anhydroglucose residual group, such as a starch or cellulose anhydroglucose residual. R is an alkylene, oxyalkylene, polyoxyalkylene, or hydroxyalkylene group, or combination thereof. R$^1$, R$^2$ and R$^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in R$^1$, R$^2$ and R$^3$) is preferably about 20 or less, and X is an anionic counterion.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimonium chloride (commercially available from Rhone-Poulenc in their JAGUAR trademark series).

Examples are JAGUAR C13S, which has a low degree of substitution of the cationic groups and high viscosity. JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the cationic conditioning polymer is selected from cationic cellulose and cationic guar derivatives. Particularly preferred cationic polymers are JAGUAR C13S, JAGUAR C15, JAGUAR C17 and JAGUAR C16 and JAGUAR C162.

The cationic conditioning polymer will generally be present in compositions of the invention at levels of from 0.01 to 5, preferably from 0.05 to 1, more preferably from 0.08 to 0.5 wt %.

Conditioning Agents

The compositions of the present invention may also contain one or more additional conditioning agents selected from silicone conditioning agents and non-silicone oily conditioning agents.

When conditioning agent is present in the compositions of the present invention in droplet form, the droplets may be liquid, semi-solid or solid in nature, so long as they are substantially uniformly dispersed in the fully formulated product. Any droplets of oily conditioning agent are preferably present as either liquid or semi-solid droplets, more preferably as liquid droplets.

Silicone Conditioning Agents

The compositions of the invention may contain emulsified droplets of a silicone conditioning agent for enhancing conditioning performance. The silicone is insoluble in the aqueous matrix of the composition and so is present in an emulsified form, with the silicone present as dispersed droplets.

Suitable silicones include polydiorganosiloxanes, in particular polydimethylsiloxanes which have the CTFA designation dimethicone. Also suitable for use compositions of the invention (particularly shampoos and conditioners) are polydimethyl siloxanes having hydroxyl end groups, which have the CTFA designation dimethiconol. Also suitable for use in compositions of the invention are silicone gums having a slight degree of cross-linking, as are described for example in WO 96/31188. These materials can impart body, volume and stylability to hair, as well as good wet and dry conditioning.

The viscosity of the emulsified silicone itself (not the emulsion or the final hair conditioning composition) is typically at least 10,000 cst. In general we have found that conditioning performance increases with increased viscosity. Accordingly, the viscosity of the silicone itself is preferably at least 60,000 cst, most preferably at least 500,000 cst, ideally at least 1,000,000 cst. Preferably the viscosity does not exceed $10^9$ cst for ease of formulation.

Emulsified silicones for use in the shampoo compositions of the invention will typically have an average silicone droplet size in the composition of less than 30, preferably less than 20, more preferably less than 10 μm. We have found that reducing the droplet size generally improves conditioning performance. Most preferably the average silicone droplet size of the emulsified silicone in the composition is less than 2 μm, ideally it ranges from 0.01 to 1 μm. Silicone emulsions having an average silicone droplet size of $\leq 0.15$ μm are generally termed microemulsions.

Suitable silicone emulsions for use in the invention are also commercially available in a pre-emulsified form. Examples of suitable pre-formed emulsions include emulsions DC2-1766, DC2-1784, and microemulsions DC2-1865 and DC2-1870, all available from Dow Corning. These are all emulsions/microemulsions of dimethiconol. Cross-linked silicone gums are also available in a pre-emulsified form, which is advantageous for ease of formulation. A preferred example is the material available from Dow Corning as DC X2-1787, which is an emulsion of cross-linked dimethiconol gum. A further preferred example is the material available from Dow Corning as DC X2-1391, which is a microemulsion of cross-linked dimethiconol gum.

A further preferred class of silicones for inclusion in shampoos and conditioners of the invention are amino functional silicones. By "amino functional silicone" is meant a silicone containing at least one primary, secondary or tertiary amine group, or a quaternary ammonium group.

Examples of suitable amino functional silicones include:
(i) polysiloxanes having the CTFA designation "amodimethicone", and the general formula:

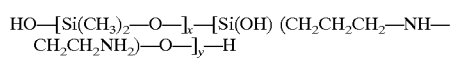

HO—[Si(CH$_3$)$_2$—O—]$_x$—[Si(OH) (CH$_2$CH$_2$CH$_2$—NH—CH$_2$CH$_2$NH$_2$)—O—]$_y$—H in which x and y are numbers depending on the molecular weight of the polymer, generally such that the molecular weight is between about 5,000 and 500,000.

(ii) polysiloxanes having the general formula:

R'$_a$G$_{3-a}$—Si (OSiG$_2$)$_n$—(OSiG$_b$R'$_{2-b}$)$_m$—O—SiG$_{3-a}$—R'$_a$ in which:
G is selected from H, phenyl, OH or $C_{1-8}$ alkyl, e.g. methyl;
a is 0 or an integer from 1 to 3, preferably 0;
b is 0 or 1, preferably 1;
m and n are numbers such that (m+n) can range from 1 to 2000, preferably from 50 to 150;
m is a number from 1 to 2000, preferably from 1 to 10;
n is a number from 0 to 1999, preferably from 49 to 149, and
R' is a monovalent radical of formula —$C_qH_{2q}L$ in which q is a number from 2 to 8 and L is an aminofuctional group selected from the following:
—NR"—CH$_2$—CH$_2$—N(R")$_2$
—N(R")$_2$
—N$^+$(R")$_3$A$^-$
—N$^+$H(R")$_2$ A$^-$
—N$^+$H$_2$(R") A$^-$
—N(R")—CH$_2$—CH$_2$—N$^+$H$_2$(R") A$^-$
in which R" is selected from H, phenyl, benzyl, or a saturated monovalent hydrocarbon radical, e.g. $C_{1-20}$ alkyl, and A is a halide ion, e.g. chloride or bromide.

Suitable amino functional silicones corresponding to the above formula include those polysiloxanes termed "trimethylsilylamodimethicone" as depicted below, and which are sufficiently water insoluble so as to be useful in compositions of the invention:

$$Si(CH_3)_3—O—[Si(CH_3)_2—O—]_x—[Si\,(CH_3)\,(R—NH—CH_2CH_2NH_2)—O—]_y—Si\,(CH_3)_3$$

wherein x+y is a number from about 50 to about 500, and wherein R is an alkylene group having from 2 to 5 carbon atoms. Preferably, the number x+y is in the range of from about 100 to about 300.

(iii) quaternary silicone polymers having the general formula:

$$\{(R^1)\,(R^2)\,(R^3)\,N^+\,CH_2CH(OH)CH_2O(CH_2)_3[Si\,(R^4)\,(R^5)—O—]_n—Si\,(R^6)\,(R^7)—(CH_2)_3—O—CH_2CH(OH)CH_2N^+\,(R^8)\,(R^9)\,(R^{10})\}\,(X^-)_2$$

wherein $R^1$ and $R^{10}$ may be the same or different and may be independently selected from H, saturated or unsaturated long or short chain alk(en)yl, branched chain alk(en)yl and $C_5$–$C_8$ cyclic ring systems;
$R^2$ thru' $R^9$ may be the same or different and may be independently selected from H, straight or branched chain lower alk(en)yl, and $C_5$–$C_8$ cyclic ring systems;
n is a number within the range of about 60 to about 120, preferably about 80, and
X$^-$ is preferably acetate, but may instead be for example halide, organic carboxylate, organic sulphonate or the like. Suitable quaternary silicone polymers of this class are described in EP-A-0 530 974.

Amino functional silicones suitable for use in shampoos and conditioners of the invention will typically have a mole % amine functionality in the range of from about 0.1 to about 8.0 mole %, preferably from about 0.1 to about 5.0 mole most preferably from about 0.1 to about 2.0 mole %. In general the amine concentration should not exceed about 8.0 mole % since we have found that too high an amine concentration can be detrimental to total silicone deposition and therefore conditioning performance.

The viscosity of the amino functional silicone is not particularly critical and can suitably range from about 100 to about 500,000 cst.

Specific examples of amino functional silicones suitable for use in the invention are the aminosilicone oils DC2-8220, DC2-8166, DC2-8466, and DC2-8950-114 (all ex Dow Corning), and GE 1149-75, (ex General Electric Silicones).

Also suitable are emulsions of amino functional silicone oils with non ionic and/or cationic surfactant.

Suitably such pre-formed emulsions will have an average amino functional silicone droplet size in the shampoo composition of less than 30, preferably less than 20, more preferably less than 10 μm. Again, we have found that reducing the droplet size generally improves conditioning performance. Most preferably the average amino functional silicone droplet size in the composition is less than 2 μm ideally it ranges from 0.01 to 1 μm.

Pre-formed emulsions of amino functional silicone are also available from suppliers of silicone oils such as Dow Corning and General Electric. Specific examples include DC929 Cationic Emulsion, DC939 Cationic Emulsion, and the non-ionic emulsions DC2-7224, DC2-8467, DC2-8177 and DC2-8154 (all ex Dow Corning).

An example of a quaternary silicone polymer useful in the present invention is the material K3474, ex Goldschmidt.

For shampoo compositions according to the invention intended for the treatment of "mixed" hair (i.e. greasy roots and dry ends), it is particularly preferred to use a combination of amino functional and non-amino functional silicone in compositions of the invention, especially when these are in the form of shampoo compositions. In such a case, the weight ratio of amino functional silicone to non-amino functional silicone will typically range from 1:2 to 1:20, preferably 1:3 to 1:20, more preferably 1:3 to 1:8.

The total amount of silicone incorporated into compositions of the invention depends on the level of conditioning desired and the material used. A preferred amount is from 0.01 to 10 wt % although these limits are not absolute. The lower limit is determined by the minimum level to achieve conditioning and the upper limit by the maximum level to avoid making the hair and/or skin unacceptably greasy.

We have found that a total amount of silicone of from 0.3 to 5, preferably 0.5 to 3 wt % is a suitable level.

The viscosity of silicones and silicone emulsions can be measured by means of a glass capillary viscometer as set out further in Dow Corning Corporate Test Method CTM004, Jul. 20, 1970.

In compositions comprising silicone, it is preferred that a suspending agent for the silicone also be present. Suitable suspending agents are as described hereinabove.

(ii) Non-silicone Oily Conditioning Components

Compositions according to the present invention may also comprise a dispersed, non-volatile, water-insoluble oily conditioning agent.

This component will be dispersed in the composition in the form of droplets, which form a separate, discontinuous phase from the aqueous, continuous phase of the composition. In other words, the oily conditioning agent will be present in the shampoo composition in the form of an oil-in-water emulsion.

By "insoluble" is meant that the material is not soluble in water (distilled or equivalent) at a concentration of 0.1% (w/w), at 250° C.

Suitably, the $D_{3,2}$ average droplet size of the oily conditioning component is at least 0.4, preferably at least 0.8, and more preferably at least 1 μm. Additionally, the $D_{3,2}$ average droplet size of the oily conditioning component is preferably no greater than 10, more preferably no greater 8, more preferably no greater than 5, yet more preferably no greater than 4, and most preferably no greater than 3.5 μm.

The oily conditioning agent may suitably be selected from oily or fatty materials, and mixtures thereof.

Oily or fatty materials are preferred conditioning agents in the shampoo compositions of the invention for adding shine to the hair and also enhancing dry combing and dry hair feel.

Preferred oily and fatty materials will generally have a viscosity of less than 5 Pa.s, more preferably less than 1 Pa.s, and most preferably less than 0.5 Pa.s, e.g. 0.1 Pa.s and under as measured at 25° C. with a Brookfield Viscometer (e.g. Brookfield RV) using spindle 3 operating at 100 rpm.

Oily and fatty materials with higher viscosities may be used. For example, materials with viscosities as high as 65 Pa.s may be used. The viscosity of such materials (i.e. materials with viscosities of 5 Pa.s and greater) can be measured by means of a glass capillary viscometer as set out further in Dow Corning Corporate Test Method CTM004, Jul. 20, 1970.

Suitable oily or fatty materials are selected from hydrocarbon oils, fatty esters and mixtures thereof.

Hydrocarbon oils include cyclic hydrocarbons, straight chain aliphatic hydrocarbons (saturated or unsaturated), and branched chain aliphatic hydrocarbons (saturated or unsaturated). Straight chain hydrocarbon oils will preferably contain from about 12 to about 30 carbon atoms. Branched chain hydrocarbon oils can and typically may contain higher numbers of carbon atoms. Also suitable are polymeric hydrocarbons of alkenyl monomers, such as $C_2$–$C_6$ alkenyl monomers. These polymers can be straight or branched chain polymers. The straight chain polymers will typically be relatively short in length, having a total number of carbon atoms as described above for straight chain hydrocarbons in general. The branched chain polymers can have substantially higher chain length. The number average molecular weight of such materials can vary widely, but will typically be up to about 2000, preferably from about 200 to about 1000, more preferably from about 300 to about 600.

Specific examples of suitable hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Exemplary branched-chain isomers are highly branched saturated or unsaturated alkanes, such as the permethyl-substituted isomers, e.g., the permethyl-substituted isomers of hexadecane and eicosane, such as 2,2,4,4,6,6,8,8-dimethyl-10-methylundecane and 2,2,4,4,6,6-dimethyl-8-methylnonane, sold by Permethyl Corporation. A further example of a hydrocarbon polymer is polybutene, such as the copolymer of isobutylene and butene. A commercially available material of this type is L-14 polybutene from Amoco Chemical Co. (Chicago, Ill., U.S.A.).

Particularly preferred hydrocarbon oils are the various grades of mineral oils. Mineral oils are clear oily liquids obtained from petroleum oil, from which waxes have been removed, and the more volatile fractions removed by distillation. The fraction distilling between 250° C. to 300° C. is termed mineral oil, and it consists of a mixture of hydrocarbons ranging from $C_{16}H_{34}$ to $C_{21}H_{44}$. Suitable commercially available materials of this type include Sirius M85 and Sirius M125, all available from Silkolene.

Suitable fatty esters are characterised by having at least 10 carbon atoms, and include esters with hydrocarbyl chains derived from fatty acids or alcohols, e.g., monocarboxylic acid esters, polyhydric alcohol esters, and di- and tricarboxylic acid esters. The hydrocarbyl radicals of the fatty esters hereof can also include or have covalently bonded thereto other compatible functionalities, such as amides and alkoxy moieties, such as ethoxy or ether linkages.

Monocarboxylic acid esters include esters of alcohols and/or acids of the formula R'COOR in which R' and R independently denote alkyl or alkenyl radicals and the sum of carbon atoms in R' and R is at least 10, preferably at least 20.

Specific examples include, for example, alkyl and alkenyl esters of fatty acids having aliphatic chains with from about 10 to about 22 carbon atoms, and alkyl and/or alkenyl fatty alcohol carboxylic acid esters having an alkyl and/or alkenyl alcohol-derived aliphatic chain with about 10 to about 22 carbon atoms, benzoate esters of fatty alcohols having from about 12 to 20 carbon atoms.

The monocarboxylic acid ester need not necessarily contain at least one chain with at least 10 carbon atoms, so long as the total number of aliphatic chain carbon atoms is at least 10. Examples include isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Di- and trialkyl and alkenyl esters of carboxylic acids can also be used. These include, for example, esters of $C_4$–$C_8$ dicarboxylic acids such as $C_1$–$C_{22}$ esters (preferably $C_1$–$C_6$) of succinic acid, glutaric acid, adipic acid, hexanoic acid, heptanoic acid, and octanoic acid. Examples include diisopropyl adipate, diisohexyl adipate, and diisopropyl sebacate. Other specific examples include isocetyl stearoyl stearate, and tristearyl citrate.

Polyhydric alcohol esters include alkylene glycol esters, for example ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol monostearate, ethoxylated propylene glycol monostearate, polyglycerol polyfatty acid esters, ethoxylated glyceryl monostearate, 1,3-butylene glycol monostearate, 1,3-butylene glycol distearate, polyoxyethylene polyol fatty acid ester, sorbitan fatty acid esters, polyoxyethylene sorbitan fatty acid esters and mono-, di-and triglycerides.

Particularly preferred fatty esters are mono-, di- and triglycerides, more specifically the mono-, di-, and triesters of glycerol and long chain carboxylic acids such as $C_1$–$C_{22}$ carboxylic acids. A variety of these types of materials can be obtained from vegetable and animal fats and oils, such as coconut oil, castor oil, safflower oil, sunflower oil, cottonseed oil, corn oil, olive oil, cod liver oil, almond oil, avocado oil, palm oil, sesame oil, peanut oil, lanolin and soybean oil. Synthetic oils include triolein and tristearin glyceryl dilaurate.

Specific examples of preferred materials include cocoa butter, palm stearin, sunflower oil, soyabean oil and coconut oil.

The oily or fatty material is suitably present at a level of from 0.05 to 10, preferably from 0.2 to 5, more preferably from about 0.5 to 3 wt %.

The compositions of this invention preferably contain no more than 3 wt % of a styling polymer, more preferably less than 1% of a styling polymer, preferably contain less than 0.1% by weight a styling polymer, and optimally are free of styling polymer.

Adjuvants

The compositions of the present invention may also contain adjuvants suitable for hair care. Generally such ingredients are included individually at a level of up to 2, preferably up to 1 wt % of the total composition.

Among suitable hair care adjuvants, are:

(i) natural hair root nutrients, such as amino acids and sugars. Examples of suitable amino acids include arginine, cysteine, glutamine, glutamic acid, isoleucine, leucine, methionine, serine and valine, and/or precursors and derivatives thereof. The amino acids may be added singly, in mixtures, or in the form of peptides, e.g. di- and tripeptides. The amino acids may also be added in the form of a protein hydrolysate, such as a keratin or collagen hydrolysate. Suitable sugars are glucose, dextrose and fructose. These may be added singly or in the form of, e.g. fruit extracts. A particularly preferred combination of natural hair root nutrients for inclusion in compositions of the invention is isoleucine and glucose. A particularly preferred amino acid nutrient is arginine.

(ii) hair fibre benefit agents. Examples are:
  ceramides, for moisturising the fibre and maintaining cuticle integrity. Ceramides are available by extraction from natural sources, or as synthetic ceramides and pseudoceramides. A preferred ceramide is Ceramide II, ex Quest. Mixtures of ceramides may also be suitable, such as Ceramides LS, ex Laboratoires Serobiologiques.

The invention will now be further illustrated by the following, non-limiting Examples:

EXAMPLES

Coated particles comprising solid silica cores and silicone coating polymer as described in JP 10144622 were used. Two types of coated particles emulsions were used, the details of which are as follows:

|  | Coated Particles I ("CPI") | Coated Particles II ("CPII") |
|---|---|---|
| Size (nm) | about 175 | about 115 (nm) |
| Wt ratio core:coating | 80:20 | 50:50 |
| Silicone coating | polydimethylsiloxane | polydimthylsiloxane |
| Solid core | colloidal silica | colloidal silica |
| Wt % of coated particles in emulsion | 20 | 20 |
| Emulsifying surfactant | Anionic | Anionic |

The following base conditioner formulations were used:

| Base A | Wt % |
|---|---|
| Cocotrimonium chloride | 0.84 |
| Distearyl dimethyl ammonium chloride | 0.375 |
| Cetostearyl alcohol | 3.00 |
| CPI or CPII | see below |
| Water, balance | to a 100% |

| Base B | Wt % |
|---|---|
| PEG-2 oleammonium chloride | 2.00 |
| Behentrimonium methosulphate | 1.00 |
| TAS | 0.75 |
| Citric acid | 0.10 |
| Cetyl alcohol | 3.00 |
| Stearyl alcohol | 2.00 |
| CPI or CPII | see below |
| Water, balance | to a 100% |

Switch Test

CPI emulsion was added to the Base A formulation as follows:

| Composition | 1: Control | 2 |
|---|---|---|
| CPI emulsion (20% active) | nil | 2.50 |

CPI emulsion was added to the Base B formulation as follows:

| Composition | 3 Control | 4 | 5 | 6 | 7 | 8 | 9 | 10 |
|---|---|---|---|---|---|---|---|---|
| CPI emulsion (20% active) | nil | 2.5 | 2.5 | 5.0 | 5.0 | 5.0 | 2.5 | 2.5 |
| Silicone DC-1786 (40% active) | nil | 0.5 | 0.1 | 1.25 | 0.5 | 0.1 | nil | nil |
| Silicone DC2-1387 (40% active) | nil | nil | nil | nil | nil | nil | 0.5 | 0.1 |

Compositions 1 and 2 and compositions 3 to 10 were tested in a hair switch test. In all cases, the compositions according to the invention beat the control compositions in the generation of hair volume.

Panel Test

CPI and CPII emulsions were added to the Base B formulation as follows:

| Composition | 3: Control | 4 | 5 |
|---|---|---|---|
| CPI emulsion (20% active) | nil | nil | 2.5 |
| CPII emulsion (20% active) | nil | 2.5 | nil |

Compositions 3, 4 and 5 were assessed in a salon half-head panel test, involving about 50 panellists. In this test, a stylist washed the whole hair with a standard shampoo. The stylist then applied one test composition to half of the head of hair, and either another test composition or the control composition to the other half of the head of hair. The hair was rinsed and the panellist asked to dry their hair as normal. The panellists were asked to evaluate a series of styling attributes associated with the body of the dried hair, each attribute being scored on a sliding numerical scale.

| Attribute | 3 | 4 | 5 |
|---|---|---|---|
| Total Panel Sample | | | |
| Easy of styling | 7.10 | 7.10 | 7.30 |
| Manageability | 6.40 | 6.80 | 7.10 |
| Body | 6.00 | 6.40 | 6.50 |
| Fullness | 5.70 | 6.10 | 6.30 |
| Bounce | 5.60 | 5.60 | 6.20 |
| Static | 2.40 | 2.00 | 1.60 |
| Flat/limp | 3.30 | 3.20 | 3.00 |
| Volume challenged panellists (i.e. with fine hair) | | | |
| Easy of styling | 6.90 | 7.50 | 7.80 |
| Manageability | 6.10 | 7.10 | 7.70 |
| Body | 5.60 | 6.70 | 6.60 |
| Fullness | 5.40 | 6.10 | 6.00 |
| Bounce | 5.40 | 5.60 | 5.60 |
| Static | 2.10 | 1.60 | 1.70 |
| Flat/limp | 3.40 | 3.20 | 3.20 |

The higher the score, the more prominent the attribute. Thus for negative attribute such as static, a lower score is preferable. Taking the results from the total sample of panellists, the compositions containing the coated particles, i.e. 4 and 5, won on most attributes, and at worst scored the same, when compared with the control composition 3. taking the results from the panellists with fine or "volume-challenged" hair, compositions 4 and 5 won on all attributes when compared with the control composition 3.

What is claimed is:

1. An aqueous conditioner composition comprising
   i) from 0.01 to 10% by weight of a cationic surfactant;
   ii) from 0.01 to 15% by weight of a fatty alcohol material; and
   iii) from 0.01 to 10% by weight of coated particles comprising
      (a) a solid core having a D3,2 average particle size in the range from 10 to 700 nm, and
      b) a coating of silicone polymer covalently bonded to the solid core.

2. A composition according to claim 1, in which the weight ratio of the solid core to the silicone coating polymer is in the range from 5:1 to 1:1.

3. A composition according to claim 1, in which the solid core comprises material selected from polymers, alumina, alumin silicate and colloidal metals.

4. A composition according to claim 1, in which the solid core is a colloidal silica.

5. A composition according to claim 1, in which the solid core particles have a Youngs Modulus of more than 0.01 GPa.

6. A composition according to claim 1, in which the silicone polymer is a polyorganosiloxane.

7. A method of imparting body to hair comprising
   i) providing an aqueous conditioner composition comprising:
      i) from 0.01 to 10% by weight of a cationic surfactant;
      ii) from 0.01 to 15% by weight of a fatty alcohol material;
      iii) from 0.01 to 10% by weight of coated particles comprising:
         (a) a solid core having a D3,2 average particle size in the range from 10 to 700 nm; and
         (b) a coating of silicone polymer covalently bonded to the solid core;
   ii) applying the conditioner to hair.

* * * * *